US00PP28897P2

(12) United States Plant Patent
Heemskerk

(10) Patent No.: US PP28,897 P2
(45) Date of Patent: Jan. 23, 2018

(54) ***HOSTA* PLANT NAMED 'SORBET'**

(50) Latin Name: *Hosta hybrida*
Varietal Denomination: Sorbet

(71) Applicant: Gerardus J. C. M. Heemskerk, Noordwijk (NL)

(72) Inventor: Gerardus J. C. M. Heemskerk, Noordwijk (NL)

(73) Assignee: HEEMSKERK VASTEPLANTEN BV, Noordwijk (NL)

( * ) Notice: Subject to any disclaimer, the term of this patent is extended or adjusted under 35 U.S.C. 154(b) by 0 days.

(21) Appl. No.: 14/999,877

(22) Filed: Jul. 13, 2016

(51) Int. Cl.
*A01H 5/12* (2006.01)

(52) U.S. Cl.
USPC ..... Plt./353

(58) Field of Classification Search
USPC ..... Plt./353
CPC ..... A01H 5/12; A01H 5/0272; A01H 5/02; A01H 5/00
See application file for complete search history.

*Primary Examiner* — June Hwu
(74) *Attorney, Agent, or Firm* — Penny J. Aguirre

(57) ABSTRACT

A new cultivar of *Hosta* named 'Sorbet' that is characterized by its petioles that are red in color and dots on the center vein of the leaf that are red in color, its leaf margins that are creamy white in color, its variegation that is varied green in color throught the leaf centers, and its late blooming period.

3 Drawing Sheets

Botanical classification: *Hosta hybrida.*
Cultivar designation: 'Sorbet'.

BACKGROUND OF THE INVENTION

The present invention relates to a new and distinct cultivar of *Hosta*, botanically known as a *Hosta hybrid* 'Sorbet' and is hereinafter referred to by its cultivar name 'Sorbet'.

The new cultivar was discovered by the Inventor in July of 2015 as a naturally-occuring chimeral mutation of *Hosta* 'Raspberry Sundae' (U.S. Plant Pat. No. 22,685) that was field grown in Noordwijk, The Netherlands.

Asexual propagation of the new cultivar was first accomplished by tissue culture using meristematic tissue under the direction of the Inventor in Heerhugowaard, Holland in July of 2016. Asexual propagation of the new cultivar by tissue culture and division has shown that the unique features are stable and reproduced true to type in successive generations.

SUMMARY OF THE INVENTION

The following traits have been repeatedly observed and represent the characteristics of the new cultivar. These attributes in combination distinguish 'Sorbet' as a new and unique cultivar of *Hosta.*

1. 'Sorbet' exhibits petioles that are red in color and dots on the center vein of the leaf that are red in color.
2. 'Sorbet' exhibits leaf margins that are creamy white in color.
3. 'Sorbet' exhibits variegation that is varied green in color throughout the leaf centers.
4. 'Sorbet' exhibits a late blooming period.

The parent plant, 'Raspberry Sundae' differs from 'Sorbet' in having variegated leaves that are reverse; margins that are green in color and and centers are creamy white in color. 'Sorbet' can be most closely compared to the *Hosta* cultivars 'Cherry Berry' (not patented) and 'Gooseberry Sundae' (not patented). 'Cherry Berry' differs from 'Sorbet' in having the reverse variegation (white centers and green margins), petioles that are less red in color and leaf blades that are smaller in size. 'Gooseberry Sunday' is similar to 'Sorbet' in having very red petioles. 'Gooseberry' differs from 'Sorbet' in having leaves that are solid green in color.

BRIEF DESCRIPTION OF THE DRAWINGS

The accompanying colored photographs illustrate the overall appearance and distinct characteristics of the new *Hosta*. The photographs were taken of 2 year-old plants as grown as grown in a glass greenhouse in a 19-cm container in Noordwijk, The Netherlands.

Figure 1:
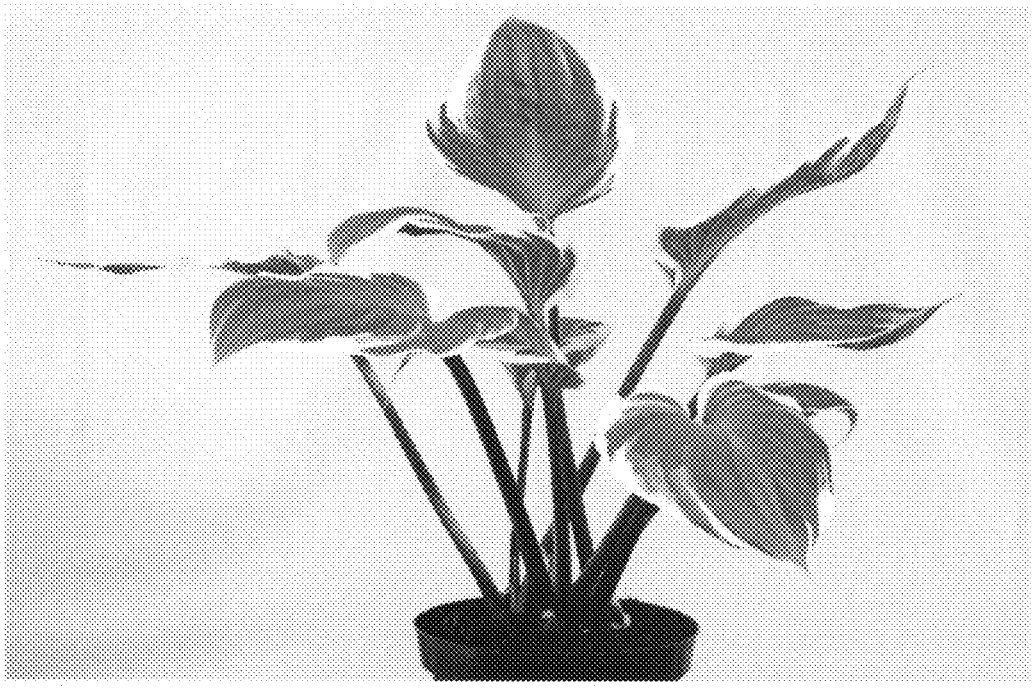
FIG. 1 provides an overall view of the plant of 'Sorbet'.
Figure 2:
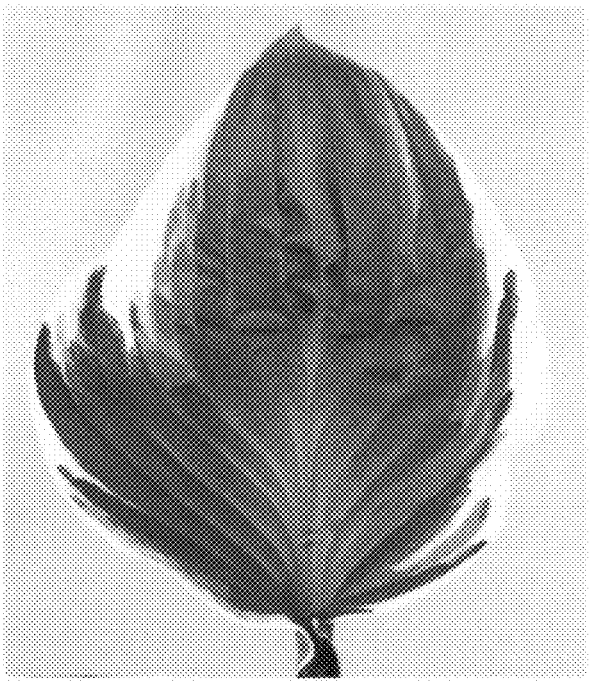

The photograph in FIG. 2 provides a close-up view of a leaf of 'Sorbet'.

Figure 3:
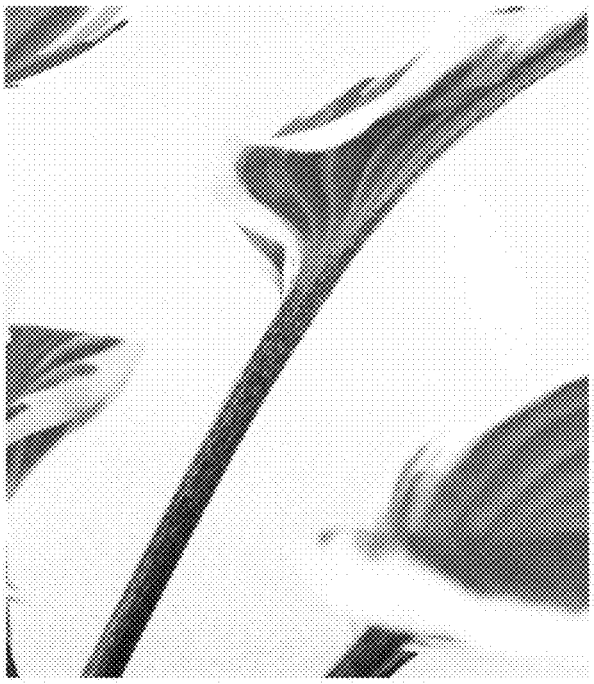

FIG. 3 provides a close-up of the petiole of 'Sorbet'.

Figure 4:
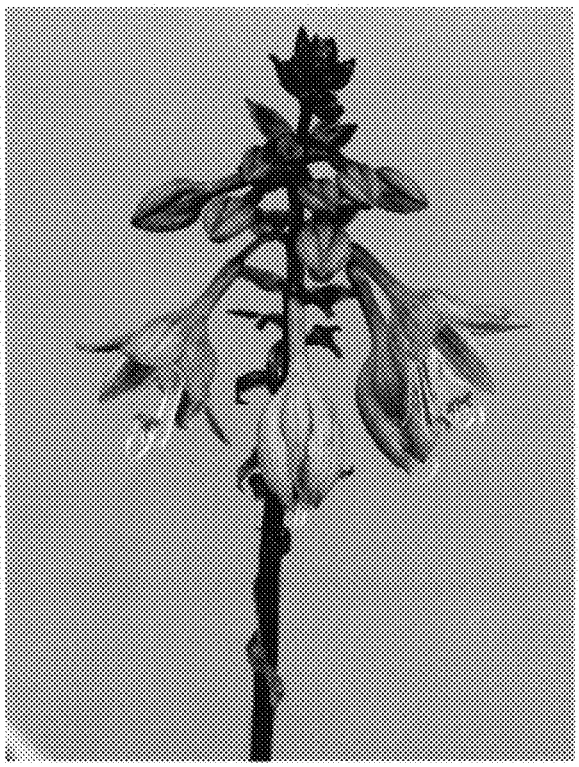

FIG. 4 provides a close-up of an inflorescence of 'Sorbet'.

Figure 5:
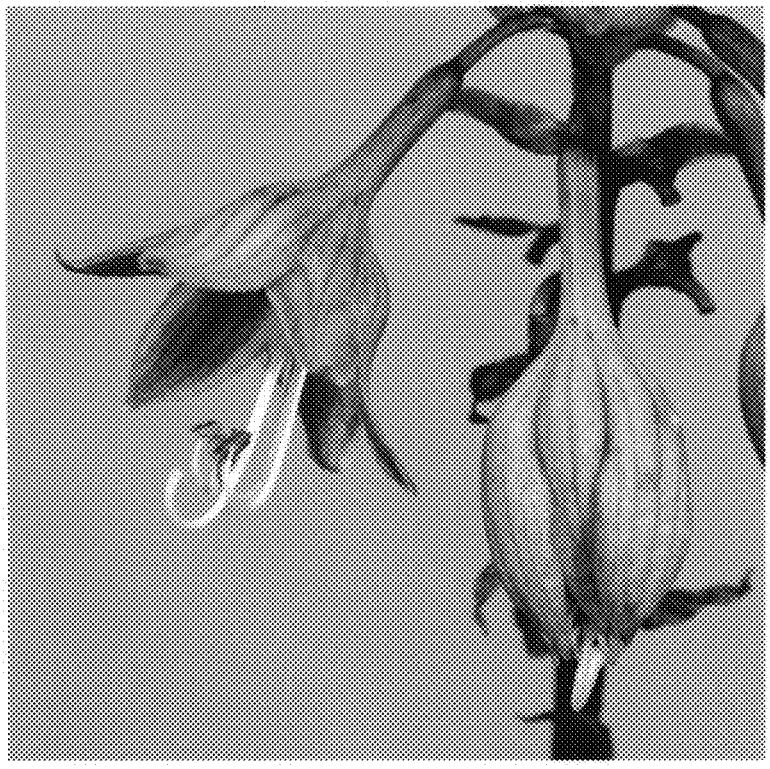

FIG. 5 provides a close-up of a flower of 'Sorbet'.

The colors in the photographs are as close as possible with the photographic and printing technology utilized and the color values cited in the Detailed Botanical Description accurately describe the colors of the new *Hosta.*

DETAILED BOTANICAL DESCRIPTION OF THE PLANT

The following is a detailed description of a 24-month-old plant of the new cultivar as grown in a 19-cm container in a glass greenhouse in Noordwijk, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Late blooming, August in The Netherlands.

*Plant type*.—Herbaceous perennial,

*Plant habit*.—Broad spreading to upright.

*Height and spread*.—An average of 39.8 cm in height and 60.5 cm in width.

*Hardiness*.—U.S.D.A. Zones 5 to 10.

*Diseases*.—No susceptibility or resistance to diseases has been observed.

*Root description*.—Freely branched, fleshy, 162D in color.

*Root development*.—About 6 months to produce a bare-root plant from a tissue culture plantlet.

*Propagation*.—Tissue culture is the preferred method utilizing typical methods for *Hosta*, division is also possible.

*Growth rate*.—Moderate.

Foliage description:

*Leaf shape*.—Ovate to broadly ovate.

*Leaf division*.—Simple.

*Leaf base*.—Truncate to cordate.

*Leaf apex*.—Apiculate.

*Leaf venation*.—Camptodrome pattern, upper surface vein color; 144A, main vein finely dotted with N186C, lower surface vein color; 144D, main vein finely dotted and blotched with 183A.

*Leaf margins*.—Entire and slightly undulate.

*Leaf attachment*.—Petiolate.

*Leaf aspect*.—Flat to slightly concave.

*Leaf arrangement*.—Alternate, in basal rosettes.

*Leaf surface*.—Upper and lower surface is glabrous, smooth, leathery and glossy.

*Leaf orientation*.—Held nearly upright to slightly outward on upright petioles.

*Leaf color*.—Young upper surface; closest to between 143A and 144A, but more contrasting and intense coloration, irregular and broadly colored margins are a blend of 10B and 147C, young lower surface; 144A, but slightly darker, irregular and broadly colored margins are a blend of 10B and 10C and 144B to 144C, mature upper surface; 143A, but slightly darker, irregular and broadly colored margins are a blend of 158C to 158D and 138B, mature lower surface; between 143A and 144A, irregular and broadly colored margins are a blend of 158C to 158D and N138C to 138D.

*Leaf size*.—Average of 22.7 cm in length and 13.8 cm in width.

*Leaf quantity*.—Average of 4 per basal rosette.

*Petioles*.—Average of 24.3 cm in length, up to 1 cm in diameter, both surfaces are glabrous and smooth surface and slightly to moderately glossy, u-shaped, strong, color upper surface; 144A to 144B, heavily blotched with 183A and slightly darker, color of lower surface; 144A, very heavily blotched with 183A and slightly darker.

Flower description:

*Inflorescence type*.—Terminal racemes of single bell-shaped flowers.

*Inflorescence size*.—18.8 cm in height, 10.5 cm in diameter.

*Lastingness of inflorescence*.—About 4 weeks from first opening bloom to fading of last opening bloom, individual blooms last up to 5 days, self cleaning.

*Flower shape*.—Campanulatc, single.

*Flower/inflorescence number*.—Average of 15 inflorescences per plant, 36 flowers per inflorescence.

*Flower fragrance*.—None.

*Flower aspect*.—Moderately drooping.

*Flower buds*.—Average of 3.5 cm in length, 1.7 cm in diameter, spathulate in shape, smooth, glabrous and glossy surface, color; 79D, striped 79B.

*Flower size*.—About 4.7 cm in height, 5.1 cm in diameter, 5.8 cm in length.

*Flower throat*.—Inner and outer surface smooth and glabrous, 6 mm in diameter, color between 85D and N155A, veins 85D.

*Flower tube*.—Average of 2.2 cm in length, 4 mm in diameter, upper and lower surface smooth and glabrous, color surface and veins 79D.

*Peduncles*.—An average of 56.7 cm in length, 6 mm in diameter, held in an average angle of 15°, moderately strong, smooth and glabrous surface, N186C in color.

*Pedicels*.—An average of 1 cm in length, 1.5 mm in diameter, held in an average angle of 70°, moderately strong, smooth and glabrous and moderately glossy surface, N79B in color.

*Calyx*.—Campanulate, 5.5 cm in length, 4.7 cm in diameter.

*Sepals*.—No Separate petals and sepals present, only tepals.

*Tepal shape*.—Oblanceolate.

*Tepal arrangement*.—Rotate, fused into a campanulate shape.

*Tepal size*.—Average of 5.5 cm in length, 1.5 mm in width.

*Tepal color*.—When opening and fully open upper surface; 79D, margined in between 85D and N155A, veins 79C, when opening and fully open lower surface; between 79D and 85A, veins 79D.

*Tepal texture*.—Upper surface; smooth and glabrous, lower surface; smooth, glabrous and slightly glossy.

*Tepal quuntity*.—6.

*Tepal margin*.—Entire.

*Tepal base*.—Fused, lower 64% fused.

*Tepal apex*.—Acute.

*Floral bracts*.—1 at the base of each pedicel, ovate in shape, apiculate apex, truncate base, both surfaces are smooth and glabrous, average of 2.4 cm in length and 1.2 cm in width, color of both surfaces N186C.

Reproductive organs:

*Gynoecium*.—Pistil; 1, 5.9 cm in length, style; 5.8 cm in length, 157D, base 79D in color, stigma; crested in shape, 1 mm in length and diameter, 150D in color, ovary is 146C to 146D, top 79A.

*Androecium*.—Stamens; 6, filament; 157B in color, 6.4 cm in length, anthers; 4 mm in length, 2 mm in width, ovate in shape, N186A in color, pollen is abundant and 15A in color.

*Fruit/seed*.—Production of seed capsules was not observed.

It is claimed:

1. A new and distinct cultivar of *Hosta* plant named 'Sorbet' as herein illustrated and described.

* * * * *